United States Patent [19]

Leonard et al.

[11] Patent Number: 4,763,529
[45] Date of Patent: Aug. 16, 1988

[54] IN-SITU BETA ALUMINA STRESS SIMULATOR

[75] Inventors: John F. Leonard, Beavercreek; Douglas M. Allen, Brookville, both of Ohio

[73] Assignee: The United States of America as represented by the Secretary of the Air Force, Washington, D.C.

[21] Appl. No.: 87,857

[22] Filed: Aug. 18, 1987

[51] Int. Cl.$^4$ ............................................. G01N 3/20
[52] U.S. Cl. ...................................... 73/852; 73/851; 73/865.6
[58] Field of Search ................. 73/788, 789, 799, 806, 73/810, 812, 849, 851, 852, 865.6; 429/90

[56] References Cited

U.S. PATENT DOCUMENTS

| | | | |
|---|---|---|---|
| 2,670,624 | 3/1954 | Faris, Jr. et al. | 73/851 |
| 3,852,114 | 12/1974 | Dubin | 136/83 |
| 4,266,424 | 5/1981 | Muensted | 73/789 |
| 4,578,325 | 3/1986 | Gatou et al. | 429/91 |
| 4,711,131 | 12/1987 | Hopkins | 73/799 |

OTHER PUBLICATIONS

Acquaviva, "A Method for Fatigue Testing of Ceramic Materials", Review of Scientific Instruments, vol. 42, No. 12, Dec. 1971.

Koning, "A Specimen for a Constant Stress Intensity Factor", Engineering Fracture Mechanics, vol. 9, pp. 331–340, 1977.

A. C. Gonzalez et al, "Fatigue Properties of Ceramics with Natural and Controlled Flaws: A Study on Alumina", ASTM STP 844:45–56(1984).

Primary Examiner—Stewart J. Levy
Assistant Examiner—Robert R. Raevis
Attorney, Agent, or Firm—Bobby D. Scearce; Donald J. Singer

[57] ABSTRACT

Method and apparatus for static fatigue testing of ceramic material is described wherein a thin plate of ceramic material is supported at opposite ends thereof in a liquid sodium bath inside an enclosure containing a gaseous atmosphere inert to reaction with liquid sodium, the ceramic plate and sodium bath are controllably heated to preselected temperature, known loads are applied to the ceramic plate through a loading head having a pair of contact points on the ceramic plate intermediate its opposite ends within the sodium bath, and displacements of the loading head at corresponding loads are measured to generate output signals characteristic of loads on the ceramic plate.

9 Claims, 1 Drawing Sheet

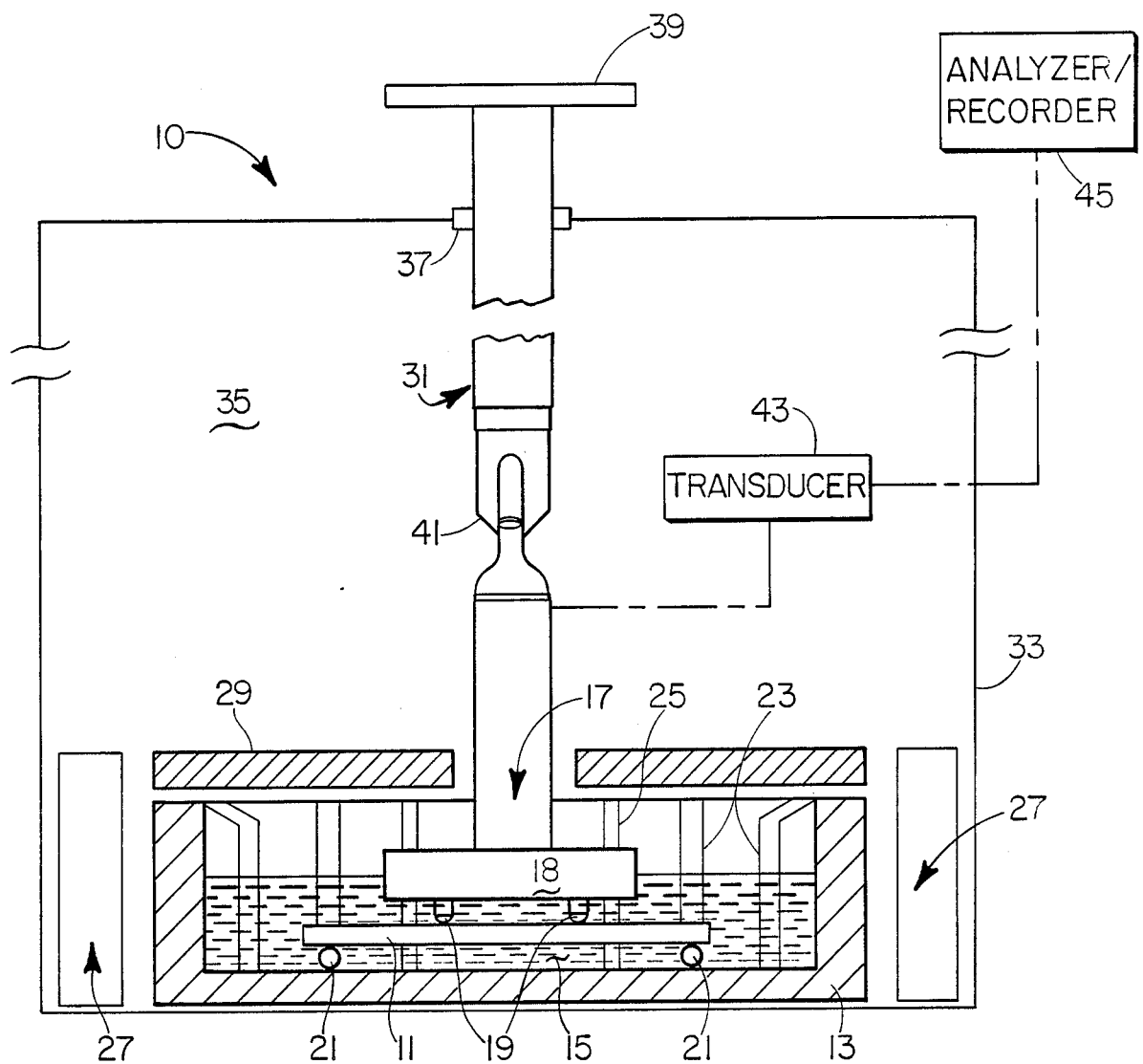

IN-SITU BETA ALUMINA STRESS SIMULATOR

RIGHTS OF THE GOVERNMENT

The invention described herein may be manufactured and used by or for the Government of the United States for all governmental purposes without the payment of any royalty.

BACKGROUND OF THE INVENTION

The present invention relates generally to testing of special materials, and more particularly to method and apparatus for static fatigue testing of beta" alumina electrolyte material in simulated sodium-sulfur battery cell conditions.

In the operation of a sodium-sulfur cell, both the sodium and sulfur are liquid at the operating temperature of the cell. Sodium ions from the liquid sodium anode are transported through a ceramic electrolyte to the liquid sulfur cathode and surrender charge in a reversible reaction with sulfur which produces sodium polysulfides. The current generated thereby is conducted through the sulfur to a metallic container which is connected to a terminal. Conventional sodium-sulfur cell structures include a solid ceramic electrolyte material which separates the sodium from the sulfur and conducts sodium ions therethrough for reaction with the sulfur. Electrolyte materials typically include beta alumina, beta" alumina, Nasicon (acronym for sodium superionic conductor containing sodium, oxygen, zirconium, silicon and phosphorus) or haloborate glasses. Beta" alumina is a preferred electrolyte material.

In the application of sodium-sulfur batteries for remote uses such as powering systems aboard orbiting satellites, the battery cell structure must have a reasonably long functional lifetime to failure. In conventional structures, failure of the cell occurs predominantly through fracture of the electrolyte. Accordingly, knowledge of structural properties and fracture mechanisms within electrolyte materials in general and within beta" alumina in particular are of critical interest in extending useful lifetimes of sodium-sulfur cells. Previous work has emphasized increase of fracture toughness of beta" alumina.

It is known that beta" alumina can fracture at subcritical stresses as a result of static fatigue. In a particular specimen of beta" alumina material, if crack growth rate increases rapidly as a function of stress intensity factor, increasing fracture toughness in the material will have no significant effect on extending the functional lifetime of electrolyte fabricated from the material. The parameters of interest most logically are, therefore, the threshold stress intensity factor (minimum stress level at which cracks can propagate), the crack growth rate as a function of stress intensity factor, and flaw size within the material from which a crack can propagate. In material having a relatively lesser steep function of crack growth rate versus stress intensity factor, fracture toughness in the material has greater affect on the life of the electrolyte.

It is therefore desirable to provide method and apparatus to mechanically test electrolyte material and more particularly beta" alumina in an environment closely simulating that of an operating sodium-sulfur battery cell incorporating the electrolyte to determine failure parameters and mechanisms of cell materials. No apparatus or method presently exists in the prior art for providing equivalent test procedures or data for electrolyte materials.

The invention meets the deficiency in the prior art just stated by providing method and apparatus for static fatigue testing of electrolyte materials, such as beta" alunina, under conditions simulating that of an operational sodium-sulfur battery. A sample of electrolyte is placed within a controlled inert atmosphere dry box in contact with liquid sodium within a controllable heater; a loading arm extending through the dry box supports a weight table external of the dry box and a loading head in contact with the sample. Transducer means connected to the loading arm measure displacement on the sample as weight is applied to the weight table to the point at which stress fracture of the sample occurs.

It is therefore a principal object of the invention to provide method and apparatus for testing ceramic electrolyte material for use in sodium-sulfur batteries.

It is another object of the invention to provide method and apparatus for testing ceramic electrolyte material under simulated conditions of an operational sodium-sulfur battery.

It is yet another object of the invention to provide method and apparatus for quality control testing of ceramic electrolyte material for a sodium-sulfur battery.

It is yet another object of the invention to provide method and apparatus for measuring physical properties of candidate ceramic electrolyte materials.

It is yet another object of the invention to provide method and apparatus for determining failure mechanisms in sodium-sulfur cells.

These and other objects of the invention will become apparent as the detailed description of representative embodiments proceeds.

SUMMARY OF THE INVENTION

In accordance with the foregoing principles and objects of the invention, method and apparatus for static fatigue testing of ceramic material is described wherein a thin plate of ceramic material is supported at opposite ends thereof in a liquid sodium bath inside an enclosure containing a gaseous atmosphere inert to reaction with liquid sodium, the ceramic plate and sodium bath are controllably heated to preselected temperature, known loads are applied to the ceramic plate through a loading head having a pair of contact points on the ceramic plate intermediate its opposite ends within the sodium bath, and displacements of the loading head at corresponding loads are measured to generate output signals characteristic of loads on the ceramic plate.

DESCRIPTION OF THE DRAWINGS

The invention will be clearly understood from the following description of representative embodiments read in conjunction with the accompanying drawing showing schematically apparatus for static fatigue testing of ceramic materials according to the invention.

DETAILED DESCRIPTION

Referring now to the drawing, shown therein is a schematic of a representative test apparatus 10 for static fatigue testing of ceramic material according to the invention. Sample 11 of ceramic electrolyte material is mounted within a container 13 in contact with bath 15 of sodium (m.p. about 97.8° C.). Sodium comprises the anode of a conventional sodium-sulfur cell employing ceramic electrolyte material exemplified by sample 11. Electrolyte within a sodium-sulfur cell normally is in the form of a thin plate or thin-walled tube a few millimeters in thickness and, accordingly, sample 11 may preferably comprise a rectangular plate of similar thickness. Loading head 17 comprising a platen 18 preferably have two or more projections 19 of preselected spacing providing a corresponding plurality of contact points with a surface of sample 11 (upper surface as shown in the drawing). In a test apparatus 10 utilized in demonstration of the invention, loading head 17 included two projections 19 for contacting sample 11, although in some tests one contact point may be sufficient. Sample 11 rests within bath 15 on a pair of supporting load pins 21 of preselected spacing for reacting at respective ends of sample 11 loads placed thereon by loading head 17. A plurality of specimen alignment pins 23 are disposed within container 13 for reproduceably positioning samples 11 within bath 15, and two pair of loading head alignment pins 25 are provided for reproduceably applying loads to samples 11. All components of loading head 17, lower load pins 21 and specimen and loading head alignment pins 23,25 comprise metal compatible with liquid sodium at the test temperatures of about 350° C. In the demonstration apparatus these components comprised stainless steel coated with 1-3 mils of chromium, although other materials such as aluminum, cold rolled steel or ceramic may be suitable as would occur to one with skill in the applicable field.

Container 13 including bath 15, sample 11, and loading head 17 are disposed within a cylindrical heater 27; a tube furnace or the like for controllably heating bath 15 to about 350° C. is suitable. Insulation 29 allowing projection therethrough of loading arm 31 operatively connected to loading head 17 provides insulation to heated bath 15 during tests. The entire assembly as just described is enclosed within dry box 33 or similar environmental enclosure containing a controlled atmosphere 35 which is inert to reaction with liquid sodium at bath 15 temperatures encountered in testing samples 11. Helium comprised the inert atmosphere in the demonstration apparatus although argon or other suitable inert gas may be used. Loading arm 31 may entend through a wall of dry box 33 at a suitable hermetic coupling as suggested at 37 and terminate at a weight table 39 or the like at which loads are controllably applied to loading head 17 in the practice of the method of the invention. Loads in torque or other non-axial loads along loading arm 31 may be relieved by including along its length a universal joint 41.

Transducer means 43 is operatively connected to loading arm 31 to measure displacements of loading head 17 corresponding to loads applied to weight table 39. In the demonstration apparatus, transducer means 43 included a linear variable differential transformer (LVDT type 1253 mfgd by Schaevitz), although other devices may be suitable. Transducer means 43 is operatively connected to analyzer and recorder electronics 45 to provide output data corresponding to differential signals from transducer means 43.

In the utilization of test apparatus 10 for fatigue testing of a ceramic electrolyte material, sample 11 of the material is placed under loading head 17 within liquid sodium bath 15 heated by heater 27 to preselected temperaure (about 350° C.) characteristic of an operating sodium-sulfur battery. Weight is applied in increments to weight table 39 in order to apply to loading head 17 a known load configuration to sample 11 at constant points of projections 19 and load pins 21. The demonstration apparatus had two projections 19 spaced at 1 cm and two load pins 21 spaced at 4 cm by which a four point bend test could be performed on sample 11 within an environment closely simulating that within a sodium-sulfur cell. Differential signals from transducer means 43 as functions of time and load indicate growth and propagation of cracks in sample 11.

Numerous samples were tested in controlled fashion in the demonstration apparatus as aforesaid in order to show operability of the invention. The samples consisted of rectangularly shaped plates of beta" alumina $45 \times 11 \times 2.5$ mm and $45 \times 11 \times 5.5$ mm formed by standard zeta process, and isostatically pressed; material of this history is conventionally used in sodium-sulfur batteries. A surface of each sample was impressed with a microhardness indentation to create a crack initiation site thereon. This procedure is according to a known method of precracking ceramics described by Gonzalez et al ("Methods for Assessing the Structural Reliability of Brittle Materials", ASTM STP 844, 43–56(1984)). Each sample was loaded to preselected stress on the indented surface and held at that stress level until failure occurred. If failure did not occur within a reasonable time (minutes to days), the stress level was increased (in about 10% increments) until failure occurred. Failure surfaces of the samples were examined in a scanning electron microscope (SEM) to determine length and shape of the resulting precrack. Test results showed that a dominant failure mode for beta" alumina is static fatigue cracking since nearly every sample failed over a period of time under an applied load but did not fail immediately.

The invention therefore teaches method and apparatus for static fatigue testing of ceramic electrolyte material under simulated operating conditions of a sodium-sulfur battery. It is understood that modifications to the invention may be made as might occur to one skilled in the field of the invention within the scope of the claims. All embodiments contemplated hereunder which achieve the objects of the invention were therefore not shown in complete detail. Other embodiments may be developed without departing from the spirit of the invention or from the scope of the claims.

We claim:

1. Apparatus for static fatigue testing of ceramic plate material comprising:
   (a) a liquid sodium bath;
   (b) means for supporting a ceramic plate at opposite ends thereof within said sodium bath;
   (c) a loading head defining at least two projections for contacting said ceramic plate within said sodium bath intermediate said opposite ends;
   (d) a furnace surrounding said sodium bath, ceramic plate and loading head for controllably heating said sodium bath and ceramic plate;
   (e) an enclosure for said sodium bath and ceramic plate containing a gaseous atmosphere substantially inert to reaction with liquid sodium;
   (f) means operatively connected to said loading head for controllably applying loads to said ceramic plate; and
   (g) measurement means operatively connected to said loading head for measuring displacements of said loading head corresponding to applied said loads and providing an output signal characteristic of said displacements.

2. The apparatus of claim 1 wherein said gaseous atmosphere comprises helium.

3. The apparatus of claim 1 wherein said gaseous atmosphere comprises argon.

4. The apparatus of claim 1 wherein said measurement means includes a linear variable differential transformer.

5. Method for static fatigue testing of ceramic plate material comprising the steps of:
(a) providing a liquid sodium bath;
(b) supporting a ceramic plate at opposite ends thereof within said sodium bath;
(c) providing a loading head defining at least two projections for contacting said sample within said sodium bath intermediate said opposite ends;
(d) enclosing said sodium bath within a gaseous atmosphere substantially inert to reaction with liquid sodium;
(e) controllably heating said sodium bath and ceramic plate;
(f) controllably applying loads to said loading head and ceramic plate; and
(g) measuring displacements of said loading head at corresponding said loads and generating an output signal characteristic of said displacements.

6. The method of claim 5 wherein said heating step is characterized by heating said sodium bath and ceramic plate to 350° C.

7. The method of claim 5 wherein said gaseous atmosphere comprises helium.

8. The method of claim 5 wherein said gaseous atmosphere comprises argon.

9. The method of claim 5 wherein said measuring step is performed using a linear variable differential transformer.

* * * * *